United States Patent [19]

Feler et al.

[11] Patent Number: 6,002,964
[45] Date of Patent: Dec. 14, 1999

[54] EPIDURAL NERVE ROOT STIMULATION

[76] Inventors: Claudio A. Feler, 950 Audubon Dr., Memphis, Tenn. 38117; Kenneth M. Alo, 4512 Teas, Bellaire, Tex. 77401

[21] Appl. No.: 09/116,185

[22] Filed: Jul. 15, 1998

[51] Int. Cl.$^6$ ..................................................... A61N 1/00
[52] U.S. Cl. ................................................................. 607/46
[58] Field of Search ................................. 607/40, 41, 43, 607/46, 117, 118

[56] References Cited

U.S. PATENT DOCUMENTS

| | | |
|---|---|---|
| 4,607,639 | 8/1986 | Tanagho et al. . |
| 4,703,755 | 11/1987 | Tanagho et al. . |
| 4,739,764 | 4/1988 | Lue et al. . |
| 4,940,065 | 7/1990 | Tanagho et al. . |
| 5,199,430 | 4/1993 | Fang et al. ................................. 607/40 |
| 5,370,670 | 12/1994 | Chancellor . |
| 5,591,724 | 1/1997 | Morales et al. . |
| 5,672,517 | 9/1997 | Domingue . |
| 5,698,549 | 12/1997 | Steers et al. . |
| 5,752,978 | 5/1998 | Chancellor . |

OTHER PUBLICATIONS

Barolat, "Percutaneous retroperitoneal stimulation of the sacral plexus", *Stereotact Funct Neurosurg*, 56(4):(1991) Abstract.

*Primary Examiner*—William E. Kamm
*Assistant Examiner*—George R. Evanisko
*Attorney, Agent, or Firm*—Sidley & Austin

[57] ABSTRACT

A method of managing chronic pain produced by a variety of disorders or conditions which afflict the pelvic region and which is transmitted through the lumbosacral region of the human body. The method includes techniques for positioning one or more stimulation leads within or about the sacrum to enable electrical energy to be applied to spinal nervous tissue, including nerve roots, to inhibit the transmission of pain.

18 Claims, 4 Drawing Sheets

EPIDURAL NERVE ROOT STIMULATION

FIELD OF THE INVENTION

The present invention relates to a method of managing human chronic pain due to disease, nervous disorders, or like afflicting the pelvic region, and in particular, to a method of applying electrical energy through electrical stimulation electrodes particularly positioned in the lumbosacral region of a patient to inhibit the transmission of chronic pain signals to the brain.

BACKGROUND OF THE INVENTION

Interstitial cystitis (IC) is a chronic inflammatory condition of unknown etiology which affects the mucosa and the muscularis of the bladder. IC is estimated to affect 450,000 people, 90% being women.

IC has a number of consistent symptoms, including hyperactive voiding and severe, debilitating pain. Current methods of treating IC or its symptoms have been largely unsuccessful. Common treatments include intravesicular instillations of medications such as heparin, dimethyl sulfoxide (for inflammation), sodium oxychlorosene (detergent), silver nitrate, and chromolymn sodium. While not offering significant improvements, these treatments themselves inflict further pain. More extreme intervention includes a cystectomy (removal of the bladder). Unfortunately, even after removal of the bladder, patients may continue to experience a level of pain consistent with that experienced prior to the procedure.

IC pain is largely visceral in nature. Visceral pain is produced in response to inflammation, distention, or increased pressure and is not necessarily due to visceral injury. Visceral pain is not well localized. IC pain may also include a neuropathic component. Consistent with some of the believed physiological understanding of IC, neuropathic pain is usually related to a nerve disruption. The pain associated with IC, being in some instances more severe than advanced cancer pain, may be intermittent or continuous.

Because of the lack of understanding of the disorder, pain management for IC is difficult. Common pain management practices currently include administering analgesic medications. For mild to moderate pain, acetaminophen, aspirin, or other nonsteroidal, antiinflammatory agents are utilized. For more severe pain, opioid medications (for example, morphine, hydromorphone, levorphanol, methadone, fentanyl, oxycodone, and hydrocodone) may be used. Of course, while opioids may provide some temporary relief, physicians must be concerned about potential side effects and the development of patient addictions.

While alternatives to opioid-only treatments exist, the success (or believed success) of the alternatives to effectively reduce that pain experienced over an extended period of time is not appreciably greater, if even greater, than that achievable through the opioid-only treatments. Alternatives to opioid use, or combinations which lessen the dependence on opioids, include: tricyclic antidepressants (offers moderate pain relief but can induce convulsions and hepatotoxicity as side effects as well as other, less severe side effects), anticonvulsants and antiarrhythmics (helpful in treating the neuropathic pain component of IC pain), and banzodiazepines. As another alternative, local anesthetics (for example, small, systemically inactive doses of opiate medications) could be applied to the bladder or pain transmitting nerves of associated with the bladder. Further alternatives may include: injection of local anaesthetics, opiates, or neurolytic agents into certain nerves using a superior hypogastric nerve block, intraspinal injection of opioids (with or without local anesthetics), intrathecal infusions of opioids (without or without local anesthetics), application of electrical stimulation external to the body (i.e., TENS stimulation), physically interrupting pain-transmitting nerves, and psychological treatments.

In addition to IC, a variety of disorders can induce chronic, severe pelvic pain of which there is no readily available treatment or answer for the symptomatic chronic severe pain. For reference, some of these conditions include, but are not limited to, lumbosacral radiculitis, lumbosacral radiculopathy, lumbosacral plexitis, lumbosacral plexopathy, vulvadynia, coccygodynia, peripheral neuritis, and peripheral neuropathy.

Accordingly, a need exists for at least a method of treating the pain produced from IC as well as other disorders which afflict the pelvic region. It is desired that the method should consciously avoid the perils of relying upon conventional drug treatments as well as avoid extreme irreversible intervention.

SUMMARY OF THE INVENTION

The present invention is drawn to a method of managing chronic pelvic pain through application of electrical energy to selected sacral nerve roots. The stimulation system includes a signal generator and at least one stimulation lead having an electrode portion and a connector portion, where the connector portion may be electrically coupled to the signal generator. The technique involves surgically implanting the at least one stimulation lead so that the electrode portion of the at least one stimulation lead lies in a plane substantially parallel to selected sacral nerve roots within the epidural space of a sacrum. Following coupling the stimulation lead to the signal generator, electrical energy is delivered from the signal generator to the electrode portion of the stimulation lead.

As one procedure for placing the electrode portion of the stimulator lead, the stimulation lead is inserted at a vertebral position superior to S1/S2 into an epidural space and advanced in an inferior direction, substantially parallel to a longitudinal direction of the epidural space, until the electrode portion reaches a desired position relative to the sacral nerve root(s).

As another procedure for placing the electrode portion of the stimulation lead, the stimulation lead is inserted through a sacral hiatus and advanced in a superior direction, substantially parallel to a longitudinal direction of the epidural space of the sacrum, until the electrode portion reaches a desired position relative to the sacral nerve root(s).

As yet another procedure for placing the electrode portion of the stimulation lead, the stimulation lead is positioned through at least a partial laminectomy of the sacrum.

An object of the present invention is to electrically stimulate selected sacral nerve roots within the epidural space of a patient to at least inhibit the transmission of pain signals from a pain-afflicted pelvic region to the brain of a patient.

Another object of the present invention is to provide a method for inserting and ultimately positioning at least one stimulation lead in a plane substantially parallel to selected nerve roots within the epidural space of a sacrum.

Another object of the present invention is to provide a method for inserting and ultimately positioning at least one stimulation lead so that an intermediate portion of the stimulation lead is within an epidural space and is largely parallel to a longitudinal axis of the epidural space, and a stimulation portion of the stimulation lead is in a plane substantially parallel to selected sacral nerve roots at a position within the epidural space of a sacrum, at a dorsal root ganglia, at a plexus, and/or at a peripheral portion thereof.

Other objects and advantages of the present invention will be apparent to those of ordinary skill in the art having reference to the following specification together with the drawings.

BRIEF DESCRIPTION OF THE DRAWINGS

FIG. 1b is a partial plan view illustrating the insertion technique of FIG. 1a;

DETAILED DESCRIPTION OF THE PREFERRED EMBODIMENTS

Application of specific electrical energy to the spinal cord for the purpose of managing pain has been actively practiced since the 1960s. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated tissue. More specifically, applying particularized electrical pulses to the spinal cord associated with regions of the body afflicted with chronic pain can induce paresthesia, or a subjective sensation of numbness or tingling, in the afflicted bodily regions. This paresthesia can effectively inhibit the transmission of non-acute pain sensations to the brain.

Electrical energy is commonly delivered through electrodes positioned external to the dura layer surrounding a spinal cord. The electrodes are carried by two primary vehicles: the percutaneous lead, which will be discussed immediately below, and the laminotomy lead, which will be discussed later.

Percutaneous leads commonly have two or more electrodes and are positioned within an epidural space through the use of a insertion, or Touhy-like, needle. An example of an eight-electrode percutaneous lead is an OCTRODE® lead manufactured by Advanced Neuromodulation Systems, Inc. of Allen, Tex.

Figure 1A:
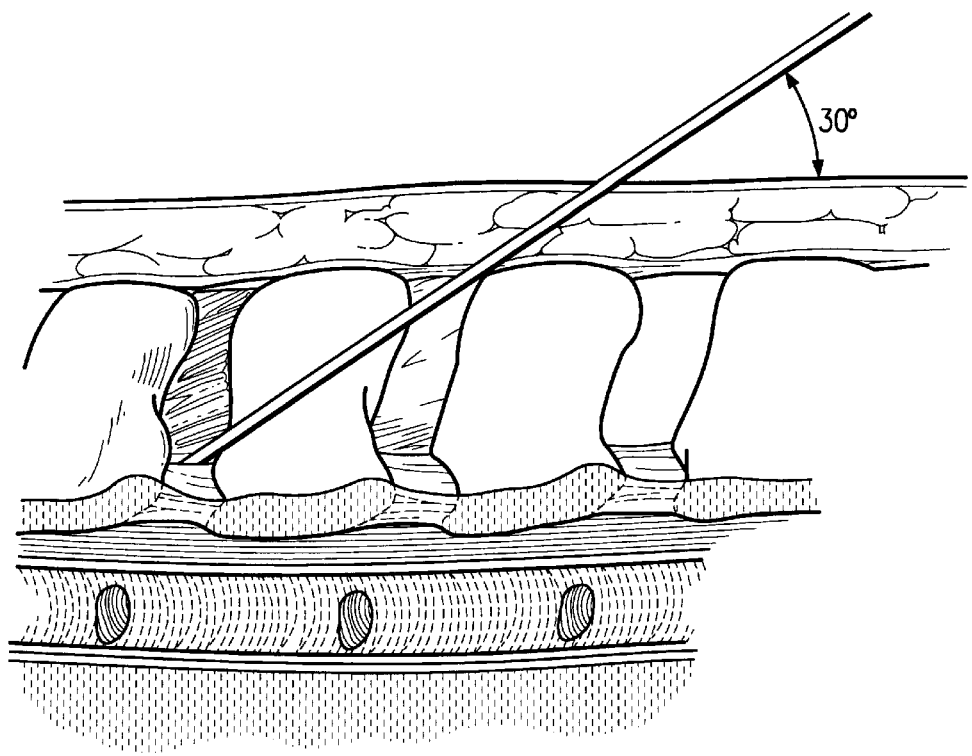
FIG. 1a is a partial, sectional side view illustrating a conventional percutaneous stimulation lead insertion technique in a rostral, or superior, direction relative to a dorsal column.
Figure 1B:
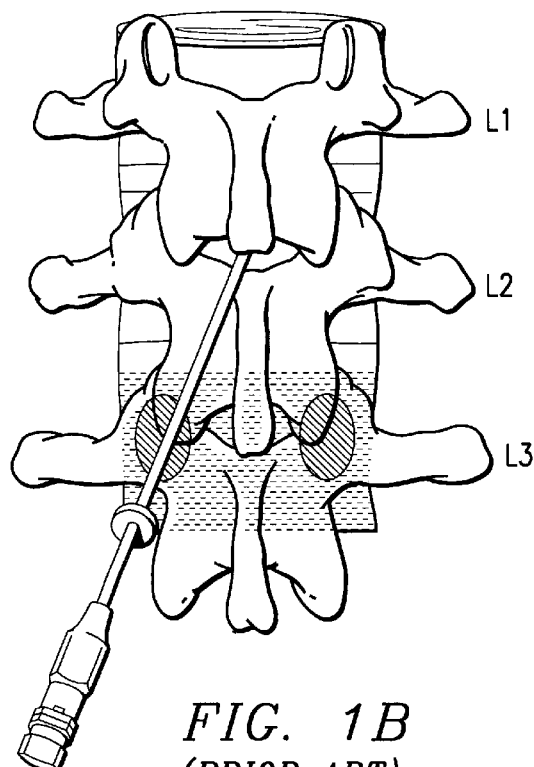

Operationally, an insertion needle is passed through the skin, between the desired vertebrae, and into an epidural space which is defined in part by the dural layer. The percutaneous lead is then fed through the bore of the insertion need and into the epidural space. Conventionally, a needle is inserted at an inferior vertebral position, for example, between vertebrae L1 and L2 (L1/L2)(see FIG. 1a and 1b), and the percutaneous lead is advanced in a superior direction, or rostrally, until the electrodes of the percutaneous lead are positioned at a desired location within the epidural space, for example, at T10. Lead placement along the vertebral tract (i.e., in a superior-inferior reference) dictates the location of applied stimulation effect, for example, lower back, extremities, or torso.

Conventional methodologies are not appropriate for effectively stimulating the region of the spinal cord or nerve roots which correspond to the pelvic region of a patient. Accordingly, the following is a method or technique for placing one or more percutaneous leads within or about the sacrum and along nerve roots associated with the pelvic region.

An insertion needle is placed between selected vertebrae in a retrograde, or caudal, direction. The needle may be inserted at any position superior to S1/S2. More preferably, the needle is inserted at L5/S1 to (and including) L1/L2. The insertion needle is guided to a depth that places the distal tip of the needle within an epidural space of the patient. As may be understood, a greater needle elevation relative to the patient is required over that for conventional needle insertion (for reference, see FIG. 1a). Once the needle is readied, a percutaneous lead is advanced through the needle (or disposable introducer), and conventional placement techniques are used to advance and to position the lead in or about the sacrum epidural space. During advancement and once positioned, a retrograde lead is largely parallel to the longitudinal direction of the receiving epidural space.

One or more percutaneous leads may be used to focus, or diversify, the electrical energy delivered by the electrodes of the percutaneous lead(s). To address pelvic pain, at least one percutaneous lead should be positioned such that it provides stimulation to the sacral nerve roots, piexi, or nerves. Specifically, a percutaneous lead should be directed from the site of insertion, through the dorsal epidural space and the sacral canal, to a position within the sacral canal or to a position which extends through a pelvic sacral foramen.

Pain which is concentrated on only one side of the body is "unilateral" in nature. To address unilateral pain, electrical energy is applied to the related neural structures lying on the same side of the patient's physiological midline as the afflicted region of the body. Pain which is present on both sides of a patient is "bilateral." Accordingly, bilateral pain is addressed through an application of electrical energy about each side of the physiological midline. Pelvic pain is commonly bilateral in nature.

As an example of this technique, the following example will concern the placement of four, four-electrode percutaneous leads. As provided above, a selected insertion site should be at least superior to S1/S2. For this example, two percutaneous leads will be inserted at T12/L1 and another two percutaneous leads will be inserted at L1/L2.

The first two leads (Lead1, Lead2) are individually inserted at L1/L2 and passed through the epidural space, including the sacral canal (or the epidural space within the sacrum). Once in the sacral canal, each of the leads may be positioned so as to span or intercept a maximum number of sacral nerve roots, where one lead is to the left and the other lead is to the right of the physiological midline. While it is likely preferable that the position of the first two leads are mirrored about the physiological midline, each patient (and their pain) is unique and may consequently require a differing configuration.

The distal end of Lead1 (and Lead2) may be positioned at approximately coccyx to approximately S1. More preferably, the distal end of Lead1 (and Lead2) may be positioned at approximately S4 to approximately S1. Most preferably, the distal end of Lead1 (and Lead2) may be positioned at approximately S4 to approximately S2. When finally positioned, the electrode portions of Lead1 and Lead2 are each in a plane parallel to one or more planes defined by the nerve roots to be stimulated.

Figure 2:
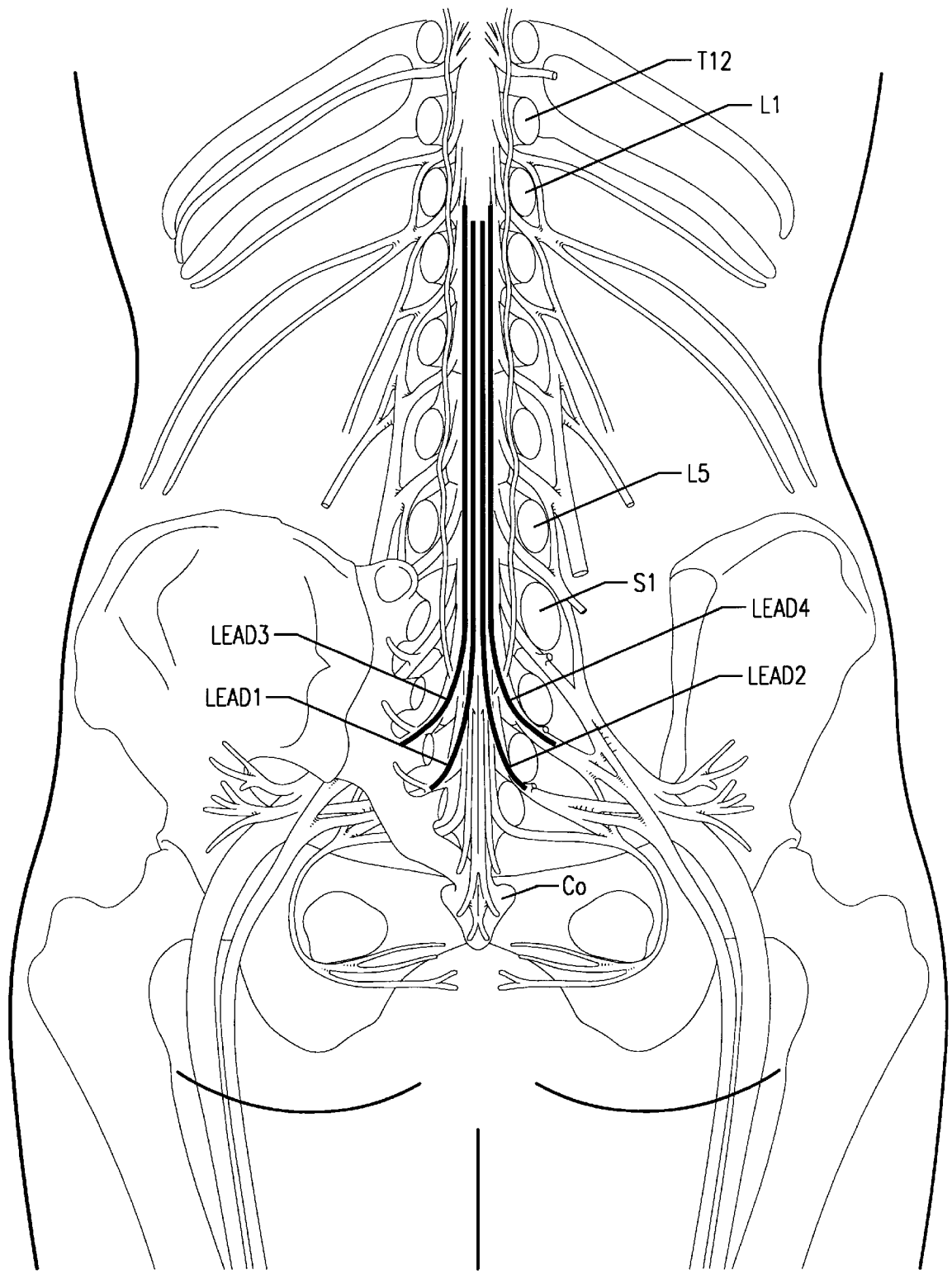
FIG. 2 is a partial, sectional view of a human body having four percutaneous stimulator leads positioned within the epidural space of a dorsal column and adjoining sacrum in accordance with the present invention.

FIG. 2 illustrates the positioning of Lead1 and Lead2. As may be seen, whether using a four electrode or an eight electrode configuration, when the percutaneous lead(s) are positioned at any of the preferred positions, a significant number of sacral nerve roots may be influenced by the electrical energy deliverable by the percutaneous leads.

The second two leads (Lead3, Lead4) are individually inserted at T12/L1 and are also passed through the dorsal epidural space to the sacral canal. Lead3 and Lead4 are first directed to the sacral canal and then passed through ventral foramina. While these leads may be passed through the S1, S3, or S4 foramina, it is preferred that the leads are positioned through the S2 foramina.

The distance between the distal tip of Lead3 (or Lead4) and the foramen in which the percutaneous lead passes dictates the scope of neural influence which may be achieved through stimulation. Specifically, spinal nerve tissue (for example, a nerve root) progresses from that within the epidural space to dorsal root (or spinal) ganglia, which exits the vertebral column, to a nerve plexus outside the vertebral column and, finally, to a more distal peripheral portion of the nerve. Accordingly, a lead may be passed through a foramen and its final position will allow all or some portion of the regions of the spinal nerve tissue to receive stimulation; provided however, the percutaneous lead includes an adequate number of electrodes, for example, four or eight electrodes, which spans the multiple portions of spinal nerve tissue.

While the above example involves four percutaneous leads, one skilled in the art shall appreciate that the number of percutaneous leads required (and their position) are dictated by the pain and physiology of each patient. One skilled in the art shall further appreciate that the order of placement of whatever the number of percutaneous leads is not a critical aspect of this invention, but rather is dependent upon the number of leads already positioned as well as patient physiology.

Figure 3:
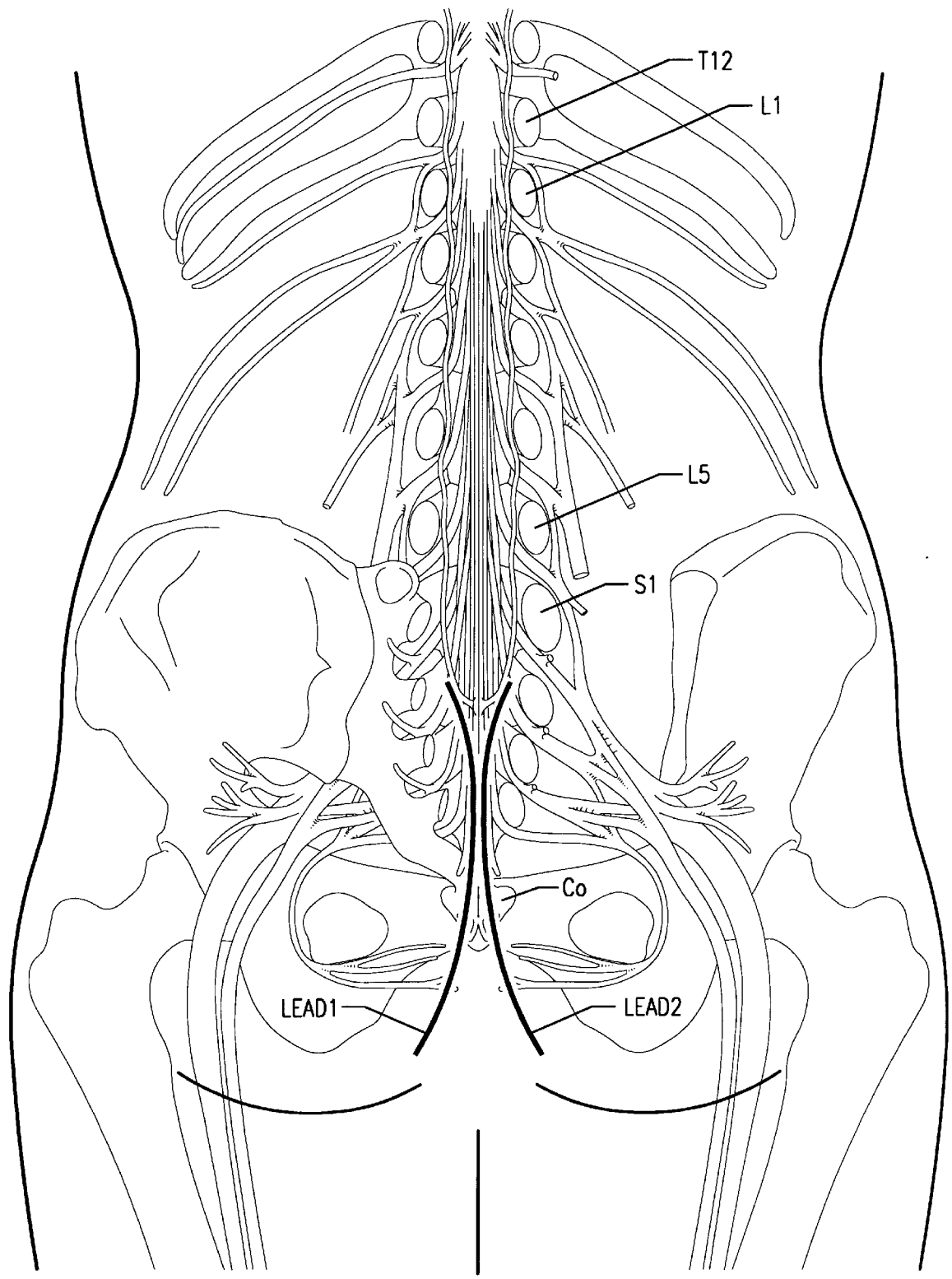
FIG. 3 is a partial, sectional view of a human body having two percutaneous stimulator leads positioned within the epidural space of a sacrum through a sacral hiatus in accordance with the present invention.

In reference to FIG. 3, a second technique for placing the electrode portion of one or more percutaneous leads in a position parallel to sacral nerve roots in or about the sacrum utilizes the sacral hiatus, or the normally-occurring gap at the lower end of the sacrum which allows cannular access to the sacral epidural space. For placement of one or more percutaneous leads, one or more leads are inserted through the sacral hiatus and passed in a superior direction through the epidural space of the sacrum to a desired location.

Laminotomy leads were mentioned above as a second means of delivering electrical energy through two or more electrodes. Unlike the needle-delivered catheter of percutaneous leads, laminotomy leads have a paddle configuration. The paddle typically possess a plurality of electrodes (for example, two, four, eight, or sixteen) arranged in some pattern, for example, columns. An example of an eight-electrode, two column laminotomy lead is a LAM-ITRODE® 44 lead manufactured by Advanced Neuromodulation Systems, Inc. of Allen, Tex.

Laminotomy leads require a surgical procedure for implantation. In the context of conventional spinal cord stimulation, the surgical procedure, or partial laminectomy, requires the resection and removal of certain vertebral tissue to allow both access to the dura and proper positioning of a laminotomy lead. Depending on the position of insertion, however, access to the dura may only require a partial removal of the ligamentum flavum at the insertion site.

Figure 4:
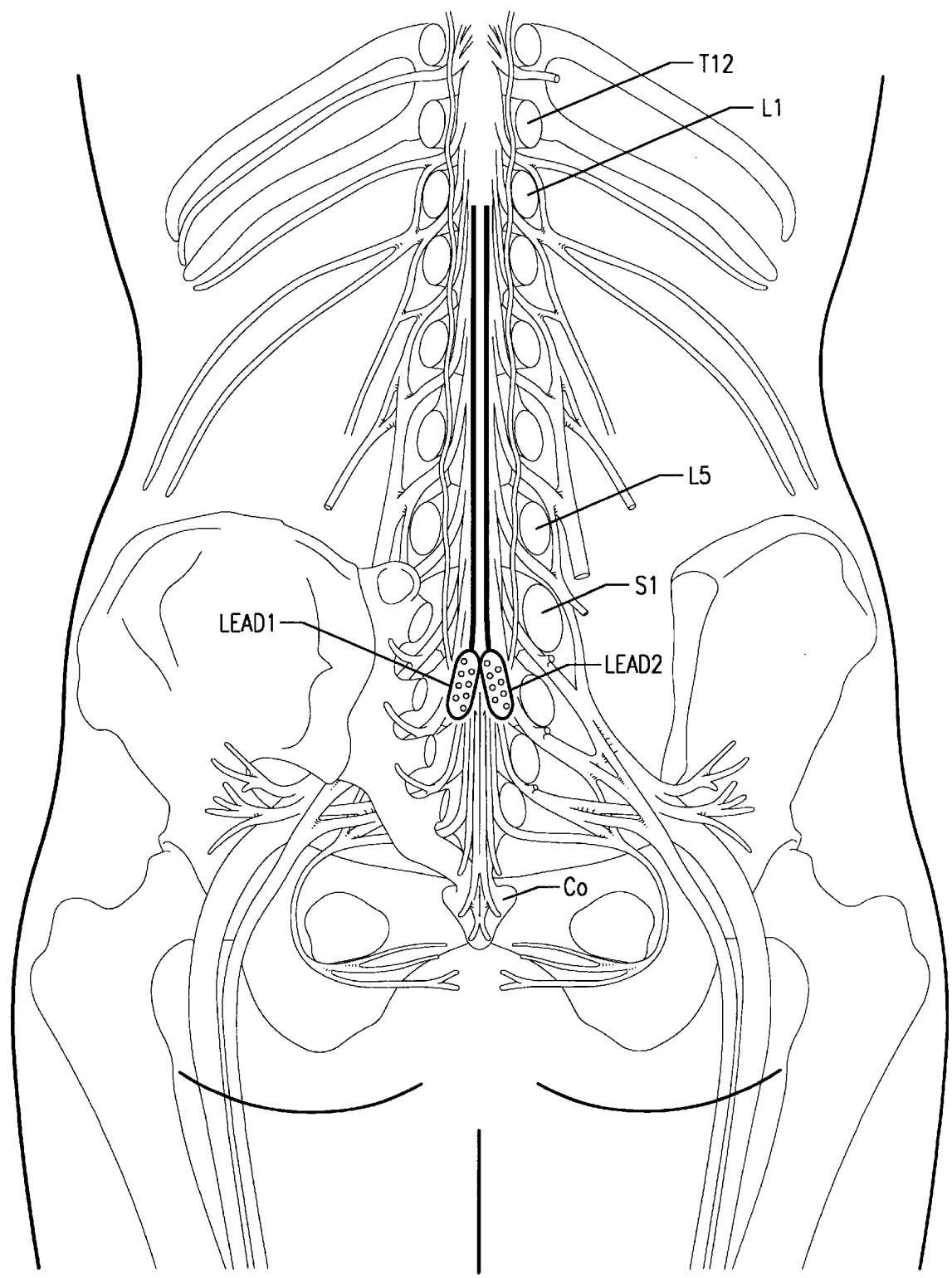
FIG. 4 is a partial, sectional view of a human body having two laminotomy stimulator leads positioned within the sacrum in accordance with the present invention.

To address pelvic pain and to position the electrodes in a plane at least parallel to the sacral nerve roots, at least a portion of the dorsal surface of the sacrum must be removed to allow access to the sacrum epidural space. Once opened, at least one laminotomy lead is positioned within the space in an orientation which allows the desired influence of sacral nerve roots when electrical energy is administered. In a preferred embodiment, two or more laminotomy leads are positioned within the sacral channel. The leads may assume any relative position to one another; however, one possible configuration would require an increasing distance between the leads from a proximal end of the leads to a distal end of the leads (see FIG. 4).

Whether using percutaneous leads, laminotomy leads, or some combination of both, the leads are coupled to one or more conventional neurostimulation devices, or signal generators. The devices can be totally implanted systems and/or radio frequency (RF) systems. An example of an RF system is a MNT/MNR-916CC system manufactured by Advanced Neuromodulation Systems, Inc. of Allen, Tex.

The preferred neurostimulation devices should allow each electrode of each lead to be defined as a positive, a negative, or a neutral polarity. For each electrode combination (i.e, the defined polarity of at least two electrodes having at least one cathode and at least one anode), an electrical signal can have at least a definable amplitude (i.e, voltage), pulse width, and frequency, where these variables may be independently adjusted to finely select the sensory transmitting nerve tissue required to inhibit transmission of pain signals. Generally, amplitudes, pulse widths, and frequencies are determinable by the capabilities of the neurostimulation systems. However, because the present invention is drawn to inhibiting transmission of signals along sensory nerves (as opposed to motor nerves), electrical signals having higher frequencies are more appropriate. Consequently, signal frequencies for this application may be between 10–25,000 Hz, and more preferably approximately 50 Hz to approximately 3,000 Hz.

While the invention has been described herein relative to a number of particularized embodiments, it is understood that modifications of, and alternatives to, these embodiments, such modifications and alternatives realizing the advantages and benefits of this invention, will be apparent those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

What is claimed is:

1. A method of managing chronic pelvic pain using a signal generator and at least one stimulation lead having an electrode portion and a connector portion, where the connector portion is electrically connectable to the signal generator, the method comprising the steps of:

surgically implanting the at least one stimulation lead so that the electrode portion of the at least one stimulation lead lies in a plane substantially parallel to selected sacral nerve roots within the epidural space of a sacrum;

coupling the at least one stimulation lead to the signal generator; and delivering electrical energy from the signal generator to the electrode portion of the at least one stimulation lead.

2. A method in accordance with claim 1, wherein a plurality of stimulation leads are implanted and coupled to at least one signal generator.

3. A method in accordance with claim 1, wherein the electrical energy has a signal frequency within the range of 50–3,000 Hz.

4. A method in accordance with claim 1, wherein the electrode portion of the at least one stimulation lead additionally extends along one or more of the following portions of the sacral nerve roots: dorsal root ganglia, sacral plexus, and peripheral nerve.

5. A method in accordance with claim 1, wherein the electrode portion of the at least one stimulation lead extends through a sacral foramen.

6. A method in accordance with claim 1, wherein the at least one stimulation lead is inserted at a vertebral position superior to S1/S2 and advanced within the epidural space in an inferior direction prior to a final position, wherein an intermediate portion of the at least one stimulation lead is substantially parallel to a longitudinal axis of the epidural space.

7. A method in accordance with claim 1, wherein the at least one stimulation lead is inserted through a sacral hiatus and advanced within the epidural space of the sacrum in a superior direction prior to a final position.

8. A method in accordance with claim 1, wherein the at least one stimulation lead is positioned through at least a partial laminectomy.

9. A method in accordance with claim 1, wherein the at least one stimulation lead is positioned through at least a partial removal of ligamentum flavum.

10. A method of managing chronic pelvic pain using at least one signal generator and at least one stimulation lead having an electrode portion and a connector portion, where the connector portion is electrically connectable to the signal generator, the method comprising the steps of:

inserting the at least one stimulation lead at a vertebral position superior to S1/S2 into an epidural space and advancing the lead in an inferior direction, substantially parallel to a longitudinal direction of the epidural space;

positioning the lead so that the electrode portion of the lead lies in a plane substantially parallel to selected sacral nerve roots within the epidural space of a sacrum;

coupling the at least one stimulation lead to the signal generator; and delivering electrical energy from the signal generator to the electrode portion of the at least one stimulation lead.

11. A method in accordance with claim 10, wherein a plurality of stimulation leads are implanted and are coupled to a plurality of signal generators.

12. A method in accordance with claim 10, wherein the electrical energy has a signal frequency within the range of 50–3,000 Hz.

13. A method in accordance with claim 10, wherein the electrode portion of the at least one stimulation lead further extends along one or more of the following portions of the selected sacral nerve roots: dorsal root ganglia, sacral plexus, and peripheral nerve.

14. A method in accordance with claim 12, wherein the electrode portion of the at least one stimulation lead extends through a sacral foramen.

15. A method of managing chronic pelvic pain using a signal generator and at least one stimulation lead having an electrode portion and a connector portion, where the connector portion is electrically connectable to the signal generator, the method comprising the steps of:

inserting the at least one stimulation lead at a vertebral position superior to S1/S2 into an epidural space and advancing the lead in an inferior direction, substantially parallel to a longitudinal direction of the epidural space;

positioning the lead so that the electrode portion of the lead lies in a plane substantially parallel to selected sacral nerve roots and is capable of directly influencing, through delivery of electrical energy, at least one of: nerve tissue within the epidural space of a sacrum, a dorsal root ganglia of the sacrum, a sacral nerve plexus, and a peripheral nerve of a pelvic region;

coupling the at least one stimulation lead to the signal generator; and delivering electrical energy from the signal generator to the electrode portion of the at least one stimulation lead.

16. A method in accordance with claim 15, wherein a plurality of stimulation leads are implanted and are coupled to a plurality of signal generators.

17. A method in accordance with claim 15, wherein the electrical energy has a signal frequency within the range of 50–3,000 Hz.

18. A method in accordance with claim 15, wherein the electrode portion of the at least one stimulation lead extends through a sacral foramen.

* * * * *